(12) United States Patent
Heath et al.

(10) Patent No.: US 11,027,861 B2
(45) Date of Patent: Jun. 8, 2021

(54) NEEDLE FREE SYRINGE AND PRE-FILLING SYSTEM

(71) Applicant: PharmaJet Inc., Golden, CO (US)

(72) Inventors: Michael Heath, Golden, CO (US); Chris Cappello, Golden, CO (US)

(73) Assignee: PharmaJet Inc., Golden, CO (US)

( * ) Notice: Subject to any disclaimer, the term of this patent is extended or adjusted under 35 U.S.C. 154(b) by 46 days.

(21) Appl. No.: 16/109,410

(22) Filed: Aug. 22, 2018

(65) Prior Publication Data

US 2018/0362194 A1  Dec. 20, 2018

Related U.S. Application Data

(63) Continuation of application No. 15/517,254, filed as application No. PCT/US2015/054294 on Oct. 6, 2015, now Pat. No. 10,065,753.
(Continued)

(51) Int. Cl.
*B65B 3/00* (2006.01)
*A61M 5/00* (2006.01)
(Continued)

(52) U.S. Cl.
CPC .............. *B65B 3/003* (2013.01); *A61M 5/002* (2013.01); *A61M 5/008* (2013.01); *A61M 5/30* (2013.01);
(Continued)

(58) Field of Classification Search
CPC ........ A61M 5/008; A61M 5/30; A61M 5/002; A61M 2005/3104; A61M 2005/3114; A61M 5/24; B65D 85/305; B65B 3/003
(Continued)

(56) References Cited

U.S. PATENT DOCUMENTS 162,285 A * 4/1875 Harris ................. B65D 85/305
217/21
210,240 A * 11/1878 Conrad ................ B65D 85/305
217/19
(Continued)

FOREIGN PATENT DOCUMENTS

WO  WO-2016-069221 A1  5/2016

OTHER PUBLICATIONS

Weniger; Bruce et al.; Alternative Vaccine Delivery Methods; National Center for Biotechnology Information; published on line at https://www.ncbi.nlm.nih.gov/pmc/articles/PMC7151876/ p. 35 (Year: 2012).*
(Continued)

*Primary Examiner* — Timothy L Maust
*Assistant Examiner* — James R Hakomaki
(74) *Attorney, Agent, or Firm* — Adsero IP

(57) ABSTRACT

Embodiments disclosed herein include needle-free syringe and cap assemblies and filling tub systems. One embodiment of filling tub system includes a filling tub having exterior walls and a floor. The floor is formed into a plurality of sockets configured to receive and support a plurality of cap and syringe body assemblies, with each cap and syringe assembly received in a separate socket. Furthermore, each socket is configured to receive and support a syringe and cap assembly with contact only between one or more surfaces of the socket and selected outer surfaces of the cap. Methods of pre-filling a quantity of needle-free syringes are also disclosed.

13 Claims, 12 Drawing Sheets

Related U.S. Application Data

(60) Provisional application No. 62/072,545, filed on Oct. 30, 2014.

(51) Int. Cl.
*A61M 5/30* (2006.01)
*A61M 5/24* (2006.01)
*A61M 5/31* (2006.01)

(52) U.S. Cl.
CPC ....... *A61M 5/24* (2013.01); *A61M 2005/3104* (2013.01); *A61M 2005/3114* (2013.01)

(58) Field of Classification Search
USPC .......................................................... 141/2
See application file for complete search history.

(56) References Cited

U.S. PATENT DOCUMENTS

| | | | | |
|---|---|---|---|---|
| 419,497 | A * | 1/1890 | Caradine | A47L 15/505 134/135 |
| 474,755 | A * | 5/1892 | Mueller | B65D 85/305 217/22 |
| 907,912 | A * | 12/1908 | Stock | B65D 85/305 220/512 |
| D98,200 | S * | 1/1936 | Worthington | A61M 5/008 D3/311 |
| 2,041,062 | A * | 5/1936 | Hale | B65D 85/305 217/19 |
| 2,588,805 | A * | 3/1952 | Cross | B65D 85/305 220/512 |
| 3,160,306 | A * | 12/1964 | Smalley | B65D 85/305 220/512 |
| 3,250,422 | A * | 5/1966 | Parish | A47G 19/2261 220/23.83 |
| 3,643,812 | A * | 2/1972 | Mander | B01L 9/06 211/74 |
| 3,897,090 | A * | 7/1975 | Maroschak | F16L 37/084 285/260 |
| 5,456,360 | A * | 10/1995 | Griffin | B01L 9/06 206/443 |
| 5,934,859 | A * | 8/1999 | Goetzelmann | A61M 5/001 294/81.52 |
| 6,048,503 | A * | 4/2000 | Riley | A61L 2/26 206/370 |
| D447,797 | S * | 9/2001 | Odell | D24/112 |
| 6,367,645 | B1 * | 4/2002 | Trygg | B65D 21/0231 220/513 |
| 6,474,481 | B1 * | 11/2002 | Liu | B25H 3/003 206/377 |
| 6,546,702 | B1 * | 4/2003 | Pickett | A61J 3/074 53/281 |
| D600,021 | S * | 9/2009 | Lindstrom | D3/313 |
| 7,937,907 | B2 * | 5/2011 | Fleckenstein | B65B 39/14 53/268 |
| D688,869 | S * | 9/2013 | Lindstrom | D3/311 |
| D694,907 | S * | 12/2013 | Okihara | D24/230 |
| D726,305 | S * | 4/2015 | Furukawa | D24/114 |
| D744,341 | S * | 12/2015 | Prince | D9/456 |
| D750,975 | S * | 3/2016 | Prince | D9/758 |
| D793,252 | S * | 8/2017 | Prince | D9/755 |
| 2002/0069616 | A1 | 6/2002 | Odell et al. | |
| 2002/0072714 | A1 | 6/2002 | Epstein et al. | |
| 2002/0170867 | A1 * | 11/2002 | Liu | B01L 9/06 211/74 |
| 2007/0151882 | A1 * | 7/2007 | Cocheteux | A61M 5/008 206/366 |
| 2012/0080342 | A1 | 4/2012 | Finke | |
| 2012/0103861 | A1 * | 5/2012 | Song | A61B 50/33 206/563 |
| 2012/0118777 | A1 * | 5/2012 | Kakiuchi | B65D 25/108 206/366 |
| 2013/0048531 | A1 * | 2/2013 | Nicoletti | A61M 5/002 206/557 |
| 2013/0164189 | A1 | 6/2013 | Hadden | |
| 2013/0186793 | A1 * | 7/2013 | Gagnieux | A61M 5/002 206/364 |
| 2014/0014654 | A1 * | 1/2014 | Gerner | B01L 9/06 220/23.83 |
| 2014/0102927 | A1 | 4/2014 | Liversidge | |
| 2015/0108020 | A1 * | 4/2015 | Iwase | A61M 5/008 206/365 |
| 2015/0114871 | A1 * | 4/2015 | Fitzpatrick | B01L 9/06 206/508 |
| 2015/0190566 | A1 * | 7/2015 | Okihara | A61M 5/3134 206/365 |
| 2016/0325043 | A1 * | 11/2016 | Fisher | A61M 5/1782 |
| 2016/0331900 | A1 * | 11/2016 | Wei | A61M 5/326 |
| 2017/0305580 | A1 | 10/2017 | Heath et al. | |

OTHER PUBLICATIONS

Pharmajet Media Kit (Year: 2014).*
International Search Report; PCT-US-2015-054294; dated Jan. 18, 2016.
Notice of Allowance dated May 8, 2018, U.S. Appl. No. 15/517,254, 7 pages.
Issue Notification dated Aug. 21, 2018, U.S. Appl. No. 15/517,254, 1 page.

* cited by examiner

NEEDLE FREE SYRINGE AND PRE-FILLING SYSTEM

RELATED APPLICATIONS

This application is a continuation of U.S. application Ser. No. 15/517,254 filed on Apr. 6, 2017, entitled "Needle Free Syringe and Pre-Filling System", which application is a 35 U.S.C. § 371 national phase application of PCT/US15/54294 (WO 2016/069221), filed on Oct. 6, 2015, entitled "Needle Free Syringe and Pre-Filling System", which application claims the benefit of U.S. Provisional Application Ser. No. 62/072,545 filed Oct. 30, 2014; each of which is incorporated herein by reference in its entirety.

TECHNICAL FIELD

The embodiments disclosed herein relate generally to needle-free injection syringes suitable for use with automated or semi-automated pre-filling systems and methods.

BACKGROUND

Certain advantages of needle-free injection technologies have been recognized for some time. Some of the advantages of needle-free devices and methods include the absence of a needle which can intimidate a patient, and which also presents a hazard to healthcare workers. In addition, injection using a needle may increase the risk of cross-contamination between patients. Furthermore, with an injection device that employs a needle there is substantial risk of needle breakage in the tissue of a human or animal patient. The injection jet generated by a needle-free device is generally smaller in diameter than a hypodermic needle and thus, in certain instances, a needle-free injection is less painful than an injection provided by a hypodermic needle device.

Because of these and other advantages of needle-free injection, many variations of pneumatic, electronic or spring activated needle-free injection devices have been designed to provide injections to patients. Most needle-free injection devices operate by driving the injectable fluid through a fine nozzle with a piston to create a fine but high pressure jet of fluid that penetrates the skin. The above advantages of needle-free injection technology are readily appreciated in a large-scale inoculation campaign. For example, limiting the fear many patients, particularly children, have of needles can increase the percentage of patient participation in large inoculation campaigns implemented in the poorer regions of the world.

Needle-free injection systems can, in certain instances, be implemented with a needle-free syringe which is filled from a vial or otherwise filled by a healthcare professional at or near the time of injection. The use of individually filled syringes however, can delay inoculation throughput or require increased labor to achieve a given number of inoculations in a specific time frame. Alternatively, injections can be administered by healthcare professional from a relatively large supply of remotely prefilled syringes. Typically, pre-filling of a large quantity of syringes is accomplished utilizing an automated or semi-automated process.

Although a needle-free injection device can be designed to utilize either (or both) prefilled or individually filled needle-free syringes, it can be difficult to economically and accurately prepare a supply of prefilled needle-free syringe, particularly without contaminating the injection nozzle or the injectable contents during filling or transportation of the prefilled syringes to a treatment location.

The embodiments disclosed herein are directed toward overcoming one or more of the problems discussed above.

SUMMARY OF THE EMBODIMENTS

The embodiments disclosed herein relate generally to needle-free syringes and methods and systems for pre-filling a selected quantity of needle-free syringes with an injectable substance. Certain embodiments disclosed herein include a needle-free syringe and filling tub system. The system comprises a plurality of syringe bodies. Each syringe body includes a nozzle at a nozzle end and a plunger opening at a plunger end, opposite the nozzle. Both the nozzle and the plunger opening define openings from the exterior of the syringe body to an interior chamber. The system further comprises a plurality of caps, with one cap engaged with each syringe body at the nozzle end. Each cap includes an interior surface which forms a fluid tight seal with each syringe at the nozzle opening. Each cap further comprises an exterior surface.

One system embodiment further includes a filling tub having exterior walls and a floor. In this embodiment, the floor is formed into a plurality of sockets configured to receive and support a plurality of cap and syringe body assemblies, with each cap and syringe assembly received in a separate socket. Furthermore, each socket is configured to receive and support a syringe and cap assembly with contact only between one or more surfaces of the socket and the outer surface of the cap. In addition, the floor the filling tub is perforated by a plurality of lifting bolt holes extending from an exterior surface of the floor into corresponding sockets.

In certain system embodiments, each needle-free syringe may have a skin tensioning ring formed in the syringe body surrounding the nozzle. The skin tensioning ring will typically define an outer circumferential edge. The syringe body may also define an annular ridge formed at least partly around an exterior surface of the syringe body between the skin tensioning ring and the plunger end of the syringe body. The cap may include one or more grip structures formed in an interior surface of the cap to mate with one or both of the skin tensioning ring and the annular ridge when the cap is engaged with the syringe body.

The grip structures may be configured in any manner which provides for the cap to be positively engaged with the syringe body. In certain embodiments however, the grip structures are formed to securely mount the cap to the syringe body while still facilitating cap removal without the use of tools. For example, the grip structures may comprise an array of flexible fins arranged parallel to the skin tensioning ring and the annular ridge when the cap is engaged with the syringe body. Each flexible fin may, in certain embodiments, extend only partially around a circumference of the interior surface of the cap.

In addition to supporting the cap and syringe assembly when engaged with a socket, the cap must also seal the interior of the syringe. Therefore, the cap may include a sealing extension. In one embodiment, the sealing extension engages with an inner circumference of the skin tensioning ring and with the exterior of the nozzle when the cap is engaged with the syringe body. The cap may further include a terminal indentation formed in an exterior surface of the cap which mates with an annular protrusion defined within a socket.

In alternative embodiments, the syringe and filling tub system comprises a plurality of needle-free syringes and caps as described above and a filling tub system having a separate filling tub and a removable nest which fits therein. The removable nest includes sockets as described above.

Alternative embodiments include a needle-free syringe and cap assembly as described herein.

Other alternative embodiments include methods of filling a plurality of needle-free syringes using at least one of the needle-free syringe and cap assemblies and filling tub systems described above.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The various embodiments disclosed herein relate generally to prefilled needle-free syringes and associated filling systems. As used herein, the term prefilled needle-free syringe refers to one or more needle-free syringes which are filled with an injectable therapeutic substance at a location which is remote from the location where injections are to take place. Typically, pre-filling will occur in a relatively large batch of multiple syringes utilizing an automated or semi-automated process.

For example, a relatively large quantity of prefilled syringes may be filled at a pharmaceutical manufacturing facility with a specific dosage of an injectable material and subsequently transported to a healthcare provider. The healthcare provider may then select a syringe prefilled with the desired dosage of a specific therapeutic substance, a vaccine for example, load the syringe into an appropriate injection device and deliver an injection. Therefore, the use of prefilled syringes can enhance patient safety through precise dosage control, streamline the injection process saving time and labor and thereby reducing costs. In certain embodiments, a filling system is disclosed which includes a plurality of needle-free syringes prior to (or after) being filled with an injectable substance and a filling tub or a filling tub/nest combination which supports the needle-free syringes and facilitates the processing of same during filling operations.

Figure 1:
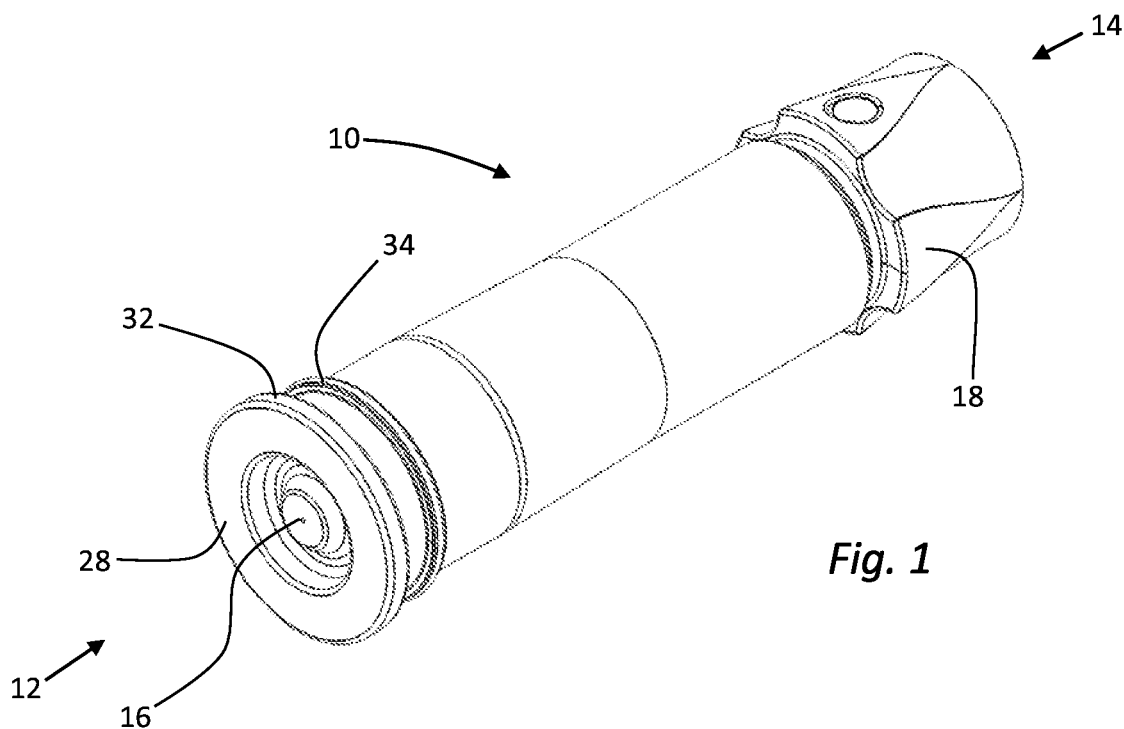
FIG. 1 is an isometric view of one embodiment of a needle-free syringe as disclosed herein.

One representative embodiment of needle-free syringe is illustrated in FIGS. 1-11. As shown in FIG. 1, a needle-free syringe 10 is a generally cylindrical device having a nozzle end 12 and a plunger end 14 opposite the nozzle end 12. The nozzle end 12 defines, among other structures, a nozzle opening 16 through which an injectable material is forced when a needle-free injection is made. Prior to an injection, the needle-free syringe 10 is loaded into a suitable injection device (not shown). The plunger end 14 of the needle-free syringe 10 includes one or more engagement structures 18 which are configured to mate with corresponding engagement structures associated with the injection device to removably attached the needle-free syringe 10 to the injection device for use. Representative, non-limiting examples of injection devices which could be used with a needle-free syringe 10 are disclosed in co-pending U.S. patent application Ser. No. 13/196,419, publication number US 2013-0035634, entitled "Needle-Free Injection Device" and co-pending U.S. patent application Ser. No. 13/711,765, publication number US 2013/0150820, entitled "Needle-Free Intradermal Injection Device." The content of each of the foregoing applications is incorporated herein by reference for all disclosures concerning the structure, operation of and functioning of needle-free injection devices including but not limited to the structure associated with said devices providing for the engagement of a needle-free syringe with the injection device.

Figure 2:
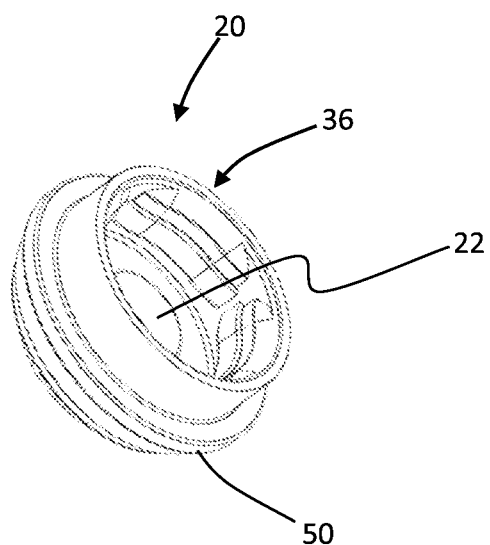
FIG. 2 is an isometric view of one embodiment of a cap configured to be mounted upon the needle-free syringe of FIG. 1.
Figure 3:
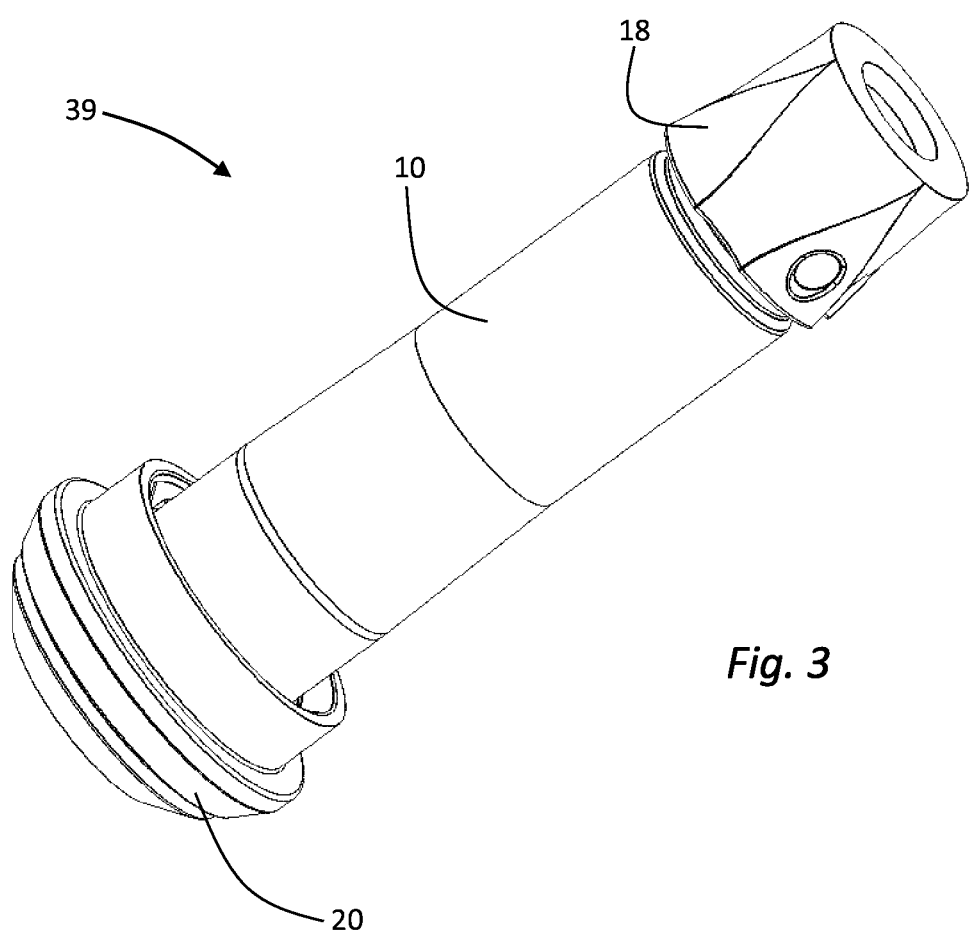
FIG. 3 is an isometric view of a needle-free syringe and cap assembly.

A prefilled needle-free syringe 10 will typically be delivered to a healthcare provider with the nozzle end 12 sealed with an appropriate cap 20. One representative cap 20 is illustrated in FIG. 2. The cap 20 is, in certain embodiments, fabricated from a pliable or elastomeric material. The cap 20 serves multiple purposes including but not limited to providing a sterile seal between the outside environment and the contents of the prefilled syringe at the nozzle 16 and supporting the prefilled syringe 10 during filling operations as described in detail below. In addition, the cap 20 may include certain structures and/or be fabricated from materials which permit a healthcare provider or other technician to easily remove the cap prior to injection without the use of tools.

Figure 5:
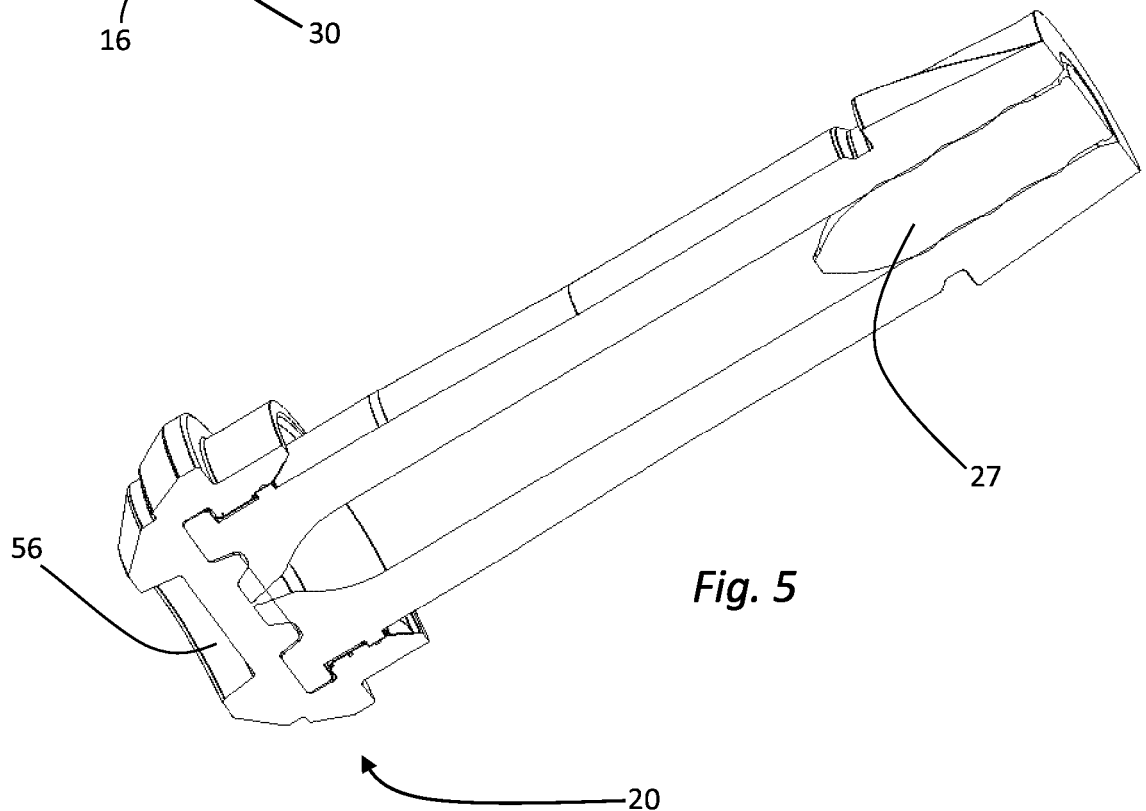
FIG. 5 is a cross-sectional view of the needle-free syringe and cap assembly of FIG. 3
Figure 6:
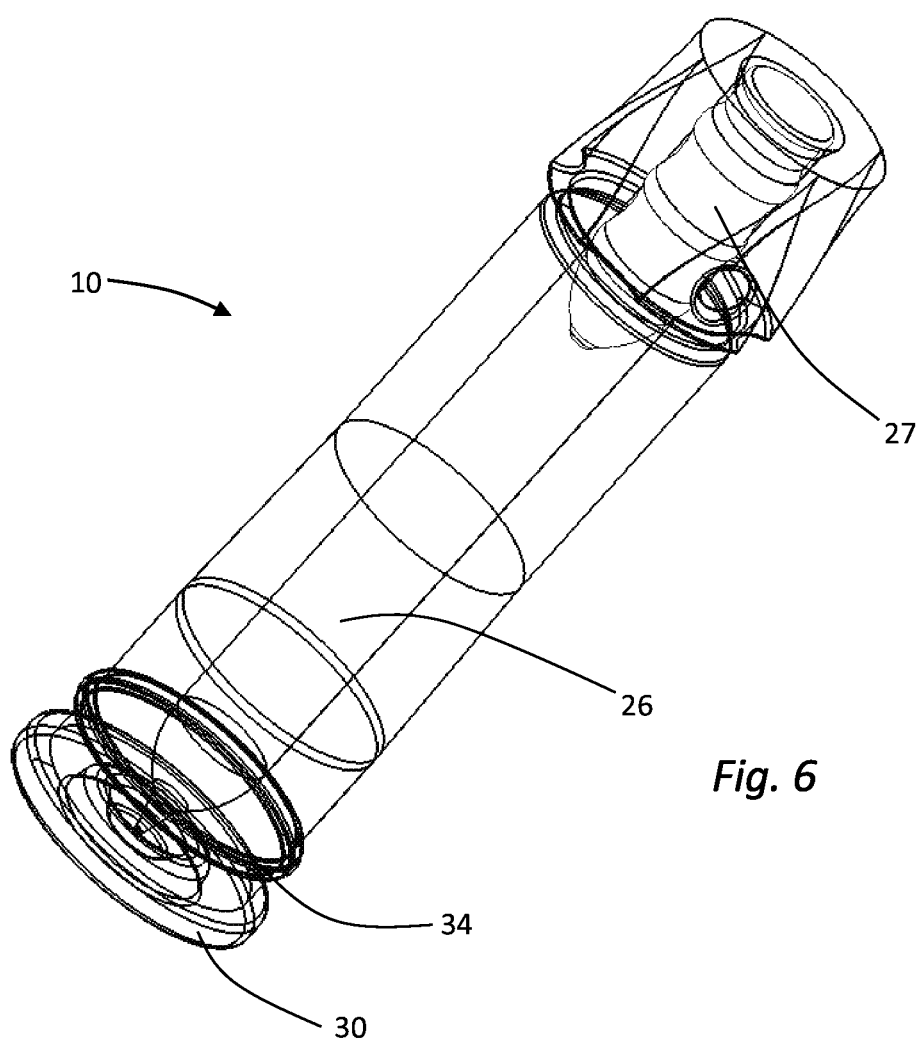
FIG. 6 is a transparent isometric rendering of the needle-free syringe of FIG. 1 showing selected internal structures.

As noted above, one purpose of the cap 20 is to provide a seal between the outside environment and the therapeutic contents of a prefilled syringe. Accordingly, a cap 20 may include a nozzle sealing extension 22 which, as best shown in FIG. 5, mates closely with the exterior nozzle surface 24 surrounding the nozzle opening 16 to prevent any leakage or contamination between the external environment and any one of the nozzle opening 16, the interior chamber 26 or an injectable material within the interior chamber 26. A plunger 27 is also illustrated in FIG. 5. As described in more detail below, the plunger 27 may be inserted into the plunger end 14 of the syringe after the interior chamber 26 is filled with a therapeutic substance, to seal the interior chamber 26 opposite the nozzle 16.

Figure 4:
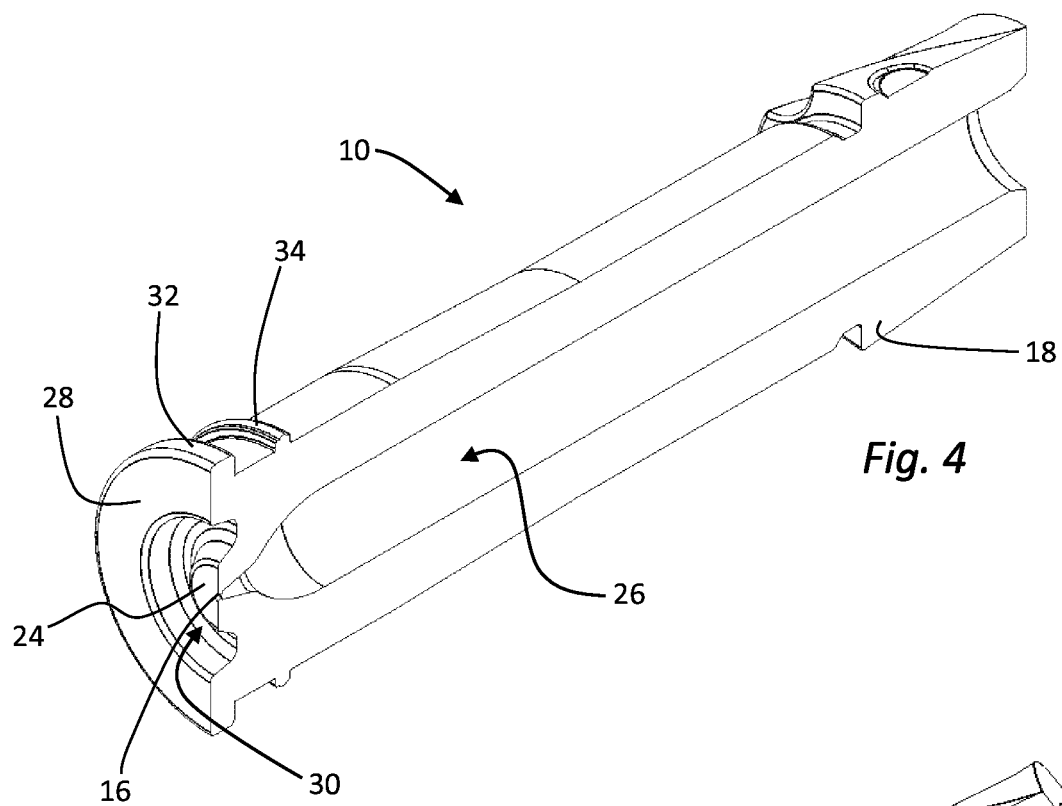
FIG. 4 is a cross-sectional view of the needle-free syringe of FIG. 1.

The needle-free syringe 10 may include certain structures at or near the nozzle end 12 which are configured to engage with the cap 20, when a cap is mounted on the syringe. For example, a needle-free syringe 10 may include an annular skin tensioning ring 28 which surrounds the nozzle opening 16 and exterior nozzle surface 24. As shown in FIG. 4, the skin tensioning ring 28 may be separated from the exterior nozzle surface 24 by an open space 30. The skin tensioning ring 28, open space 30 and exterior nozzle surface 24 are in the illustrated embodiment configured to function together, under the force applied against a patient's skin during an injection, to properly tension the patient's skin for the needle-free injection. In addition, the skin tensioning ring 28 may include a perimeter surface 32 which engages the cap 20 when the cap is mounted, as shown in FIG. 5. Thus, the perimeter surface 32 provides for a supplemental seal between the cap 20 and needle-free syringe 10.

The needle-free syringe 10 may also include an annular ridge 34 formed around the exterior of the syringe 10 distal to the skin tensioning ring 28. As shown in FIG. 5, the annular ridge 34 can provide a third region of engagement between the needle-free syringe 10 and cap 20.

Figure 7:
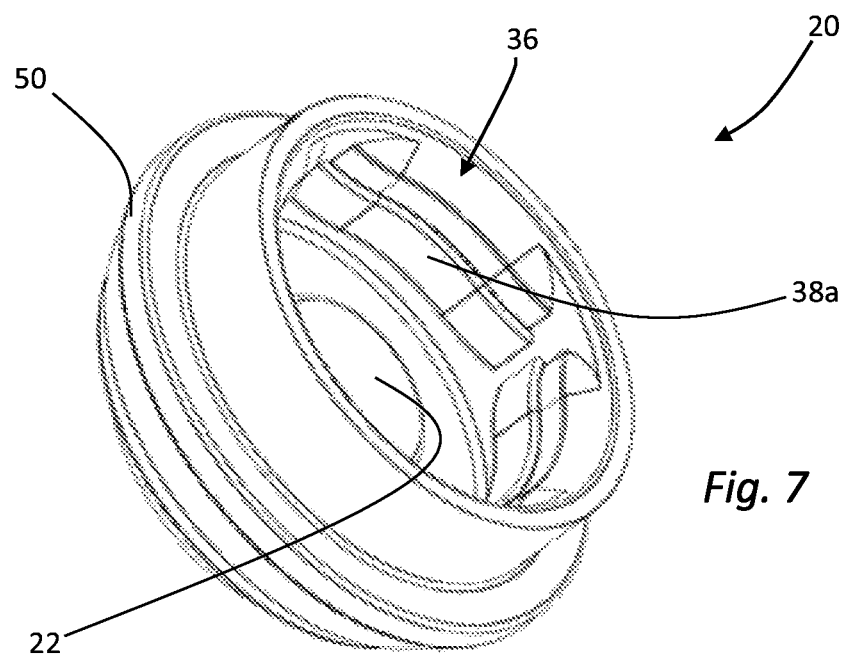
FIG. 7 is a rear isometric view of the cap of FIG. 2.
Figure 8:
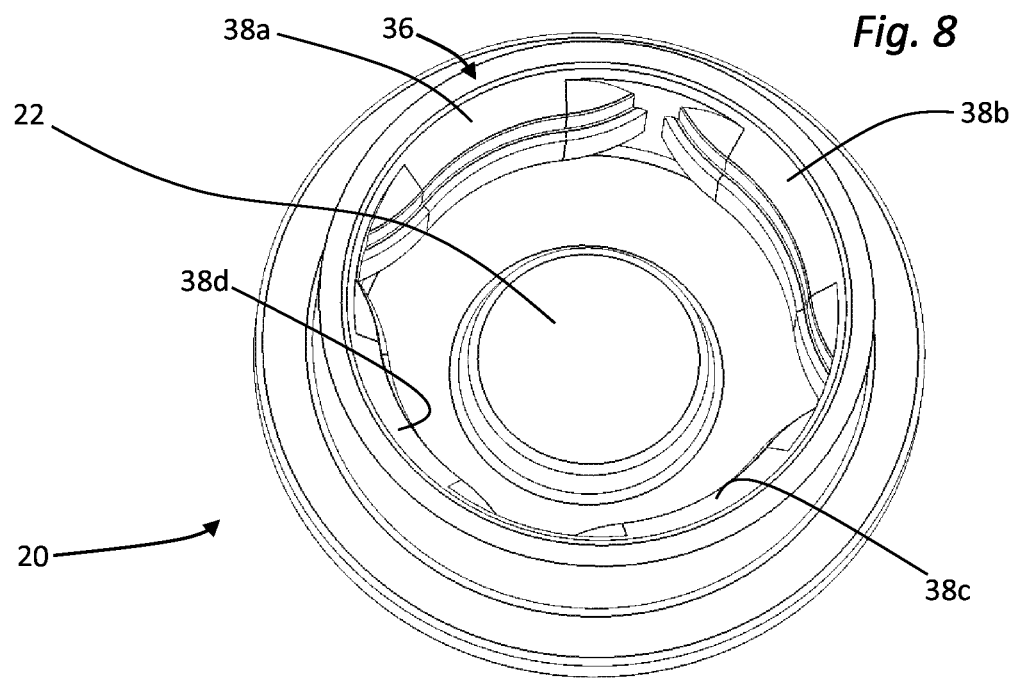
FIG. 8 is an alternative rear isometric view of the cap of FIG. 2.
Figure 9:
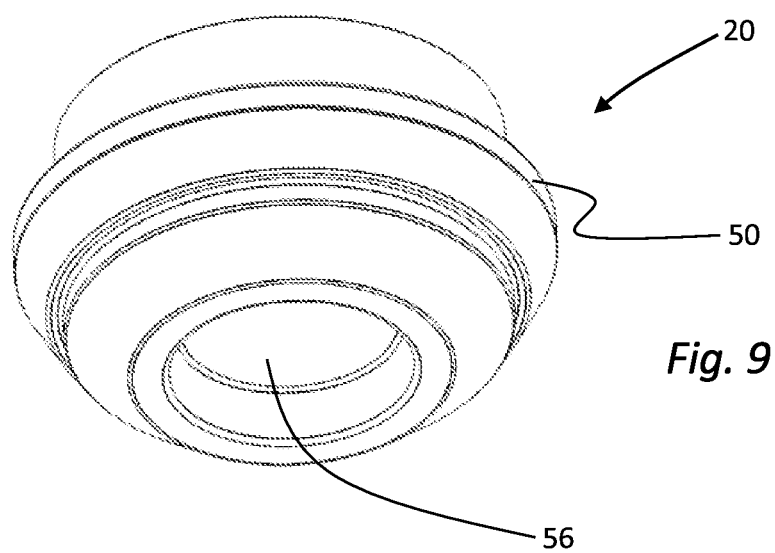
FIG. 9 is a front isometric view of the cap of FIG. 2.
Figure 10:
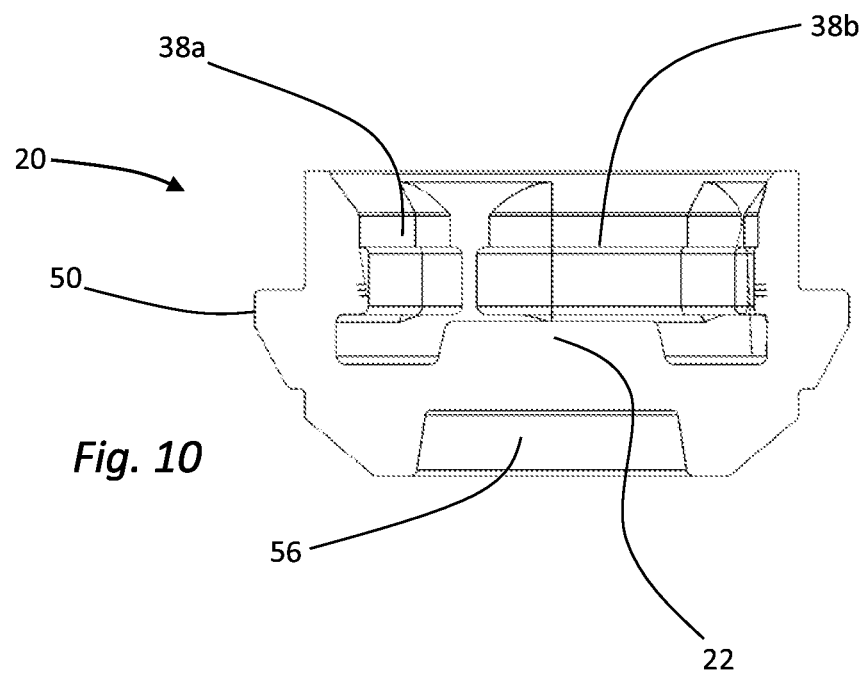
FIG. 10 is a cross-sectional view of the cap of FIG. 2.
Figure 11:
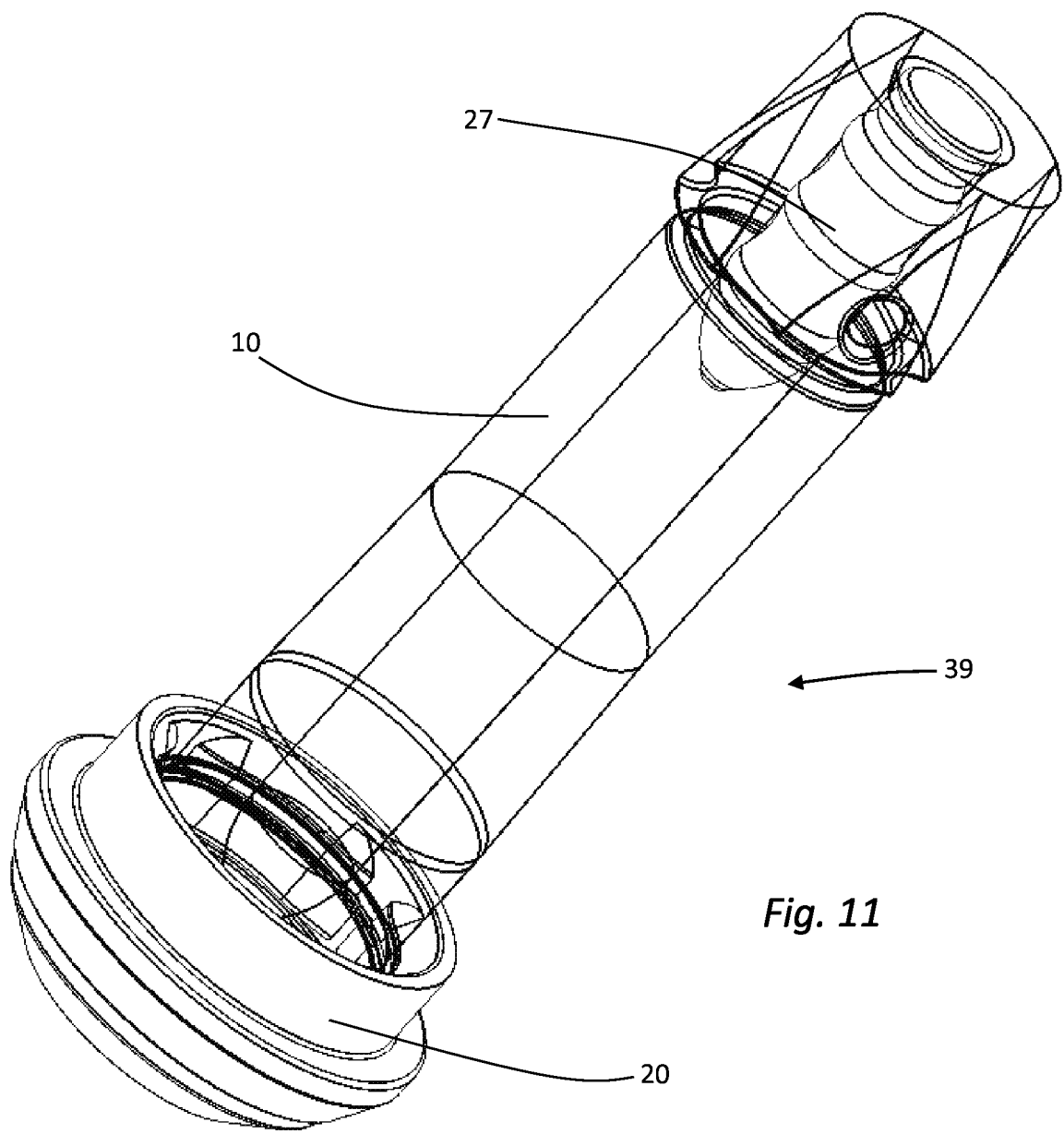
FIG. 11 is a transparent isometric rendering of the needle-free syringe and cap assembly of FIG. 3 showing selected internal structures.
Figure 12:
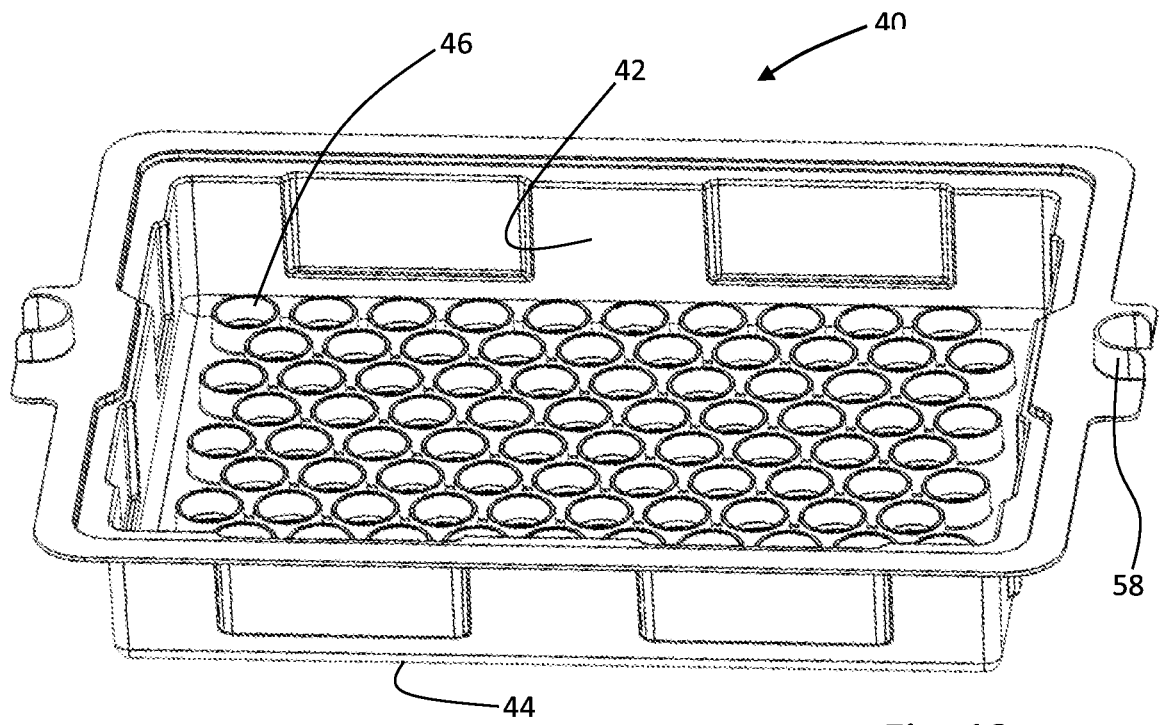
FIG. 12 is a top isometric view of one embodiment of filling tub as disclosed herein.
Figure 13:
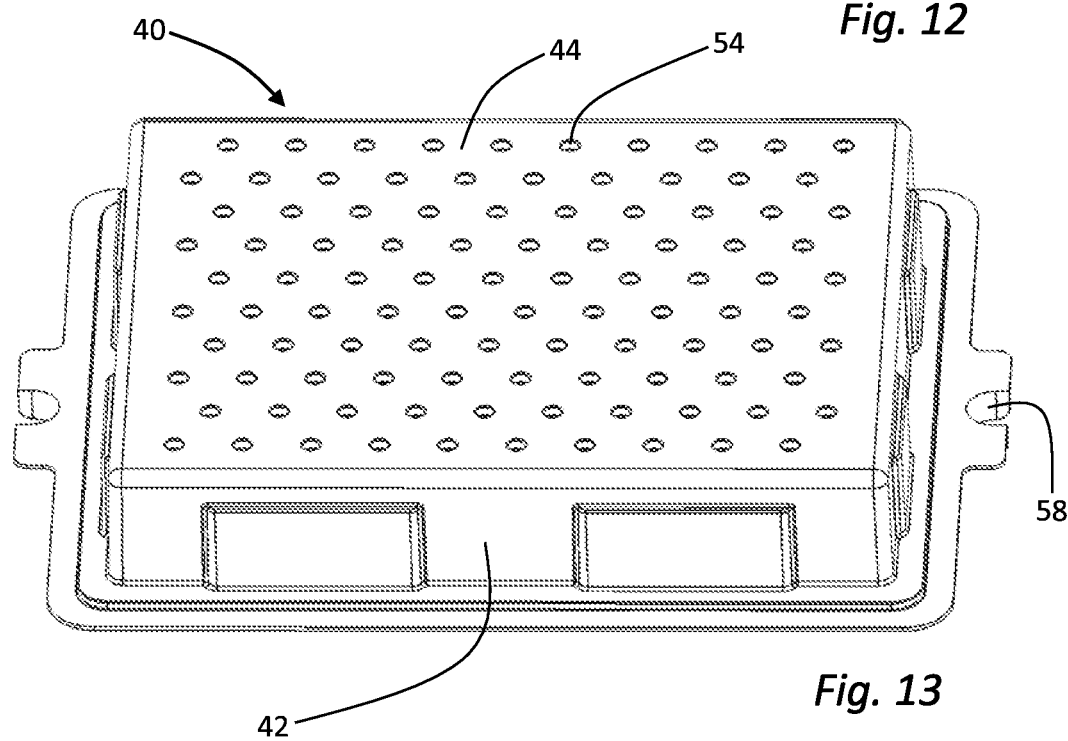
FIG. 13 is a bottom isometric view of the filling tub of FIG. 12.
Figure 14:
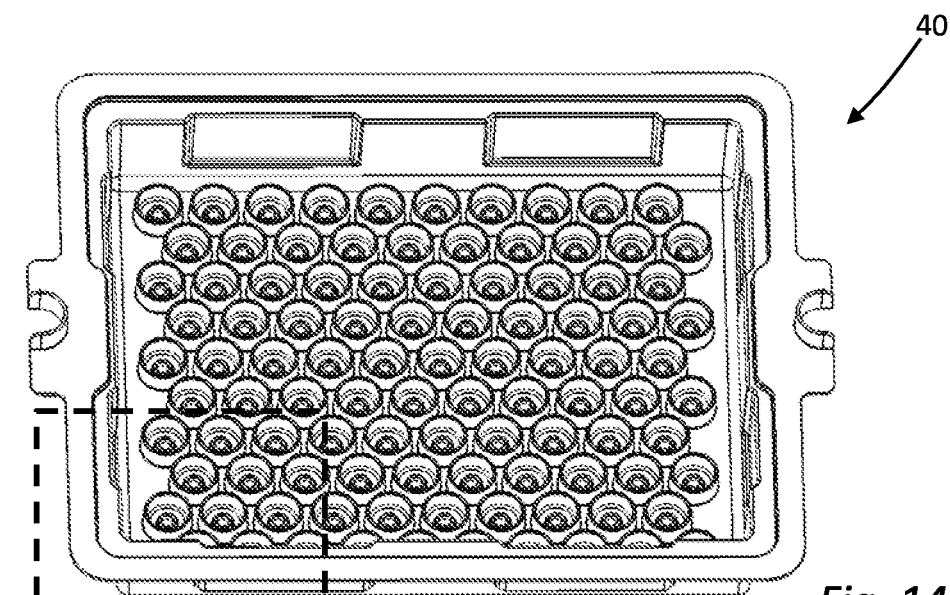
FIG. 14 is a top isometric view of the filling tub of FIG. 12.
Figure 15:
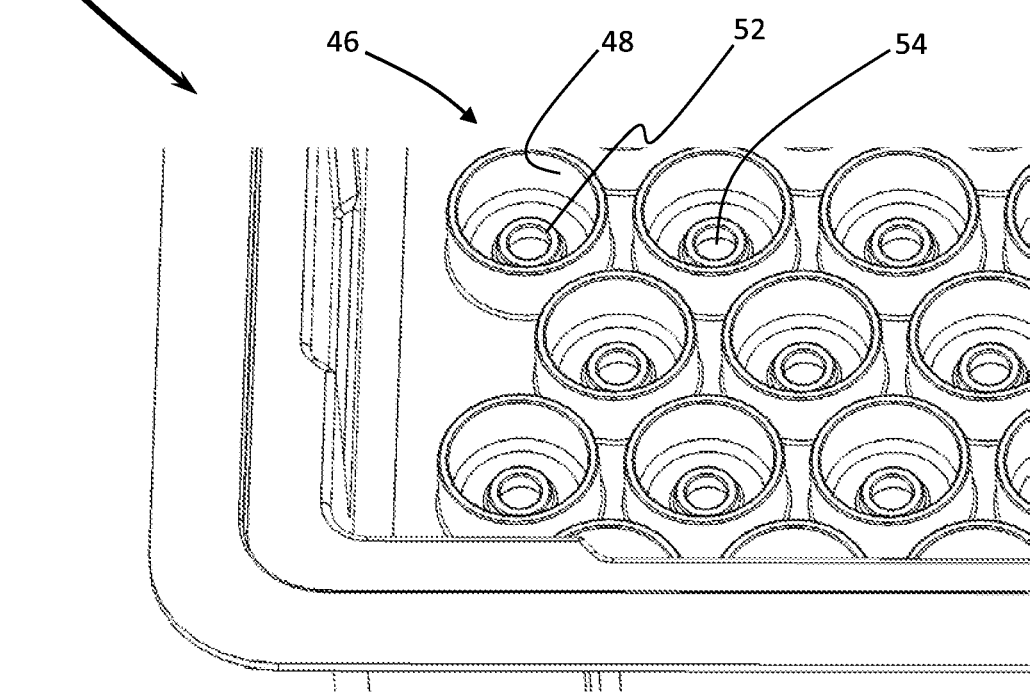
FIG. 15 is a detailed view of a portion of the filling tub of FIG. 14.

The cap 20 may also be provided with structures providing for secure engagement with the needle-free syringe 10 while, in certain instances, facilitating the removal of a cap 20 from a needle-free syringe 10 by hand or without the use of tools. For example, as shown in FIGS. 7 and 8, the cap 20 may include one or more grip structures 36. It may be observed in FIG. 2 and FIG. 5, that in certain embodiments, grip structures 36 are positioned to fit over and engage with the skin tensioning ring 28 when the cap 20 is placed on the needle-free syringe 10. In certain embodiments, the plurality of grip structures 36 comprise at least one set of co-planar flexible fins, 38a-38d. In the particular embodiment of FIG. 8, the grip structure 36 comprises four coplanar flexible fins 38a-d. In some embodiments, each grip structure 36 may comprise a stacked lengthwise array of flexible fins 38. The illustrated gap between adjacent coplanar flexible fin segments 38 facilitates the removal of the cap 20 from the needle-free syringe 10 by hand or without the use of tools by reducing the force required to peel the flexible cap 20 off of the syringe.

As noted above, the described needle-free syringe and cap assembly (referred to below as a syringe/cap assembly 39 is particularly well-suited for pre-filling. FIGS. 12-19 illustrate various embodiments of filling tub and nest systems which can be used with a plurality of needle-free cap and syringe assemblies 39 to provide for automated or semi-automated pre-filling of the syringes with a therapeutic substance. In particular FIGS. 12-17 illustrate a first embodiment which includes a one piece filling tub and nest combination, referred to herein as filling tub 40. The one piece filling tub 40 may be fabricated as a single unit by any known technique, injection molding for example. Alternatively, the one piece filling tub 40 may be assembled from multiple sub-components which are attached, bonded or otherwise affixed together prior to use.

The filling tub 40 includes exterior walls 42 and a floor 44. In the illustrated embodiment, the exterior walls and floor defined a substantially rectangular tub shape having a length, width, depth and a wholly or partially open top. The rectangular tub shape is not limiting, the filling tub 40 can be prepared in any suitable configuration. Typically, the depth of the filling tub 40 will be equal to or greater than the axial length of a cap and needle-free syringe assembly 39.

In the FIG. 12-17 embodiment the filling tub 40 includes a plurality of sockets 46 configured to receive and support a plurality of cap and syringe assemblies 39 and to engage each cap and syringe assembly 39 with contact between only selected surfaces of the socket 46 and specific outer surfaces of the cap 20. In particular, as shown in the detailed view of FIG. 15, the filling tub 40 includes a floor 44 which is formed into multiple adjacent sockets 46. Each socket 46 is configured to receive and support a cap/syringe assembly 39 during selected filling operations. In particular, each socket 46 includes a perimeter socket wall 48 which is sized to engage with a circumferential rim 50 of the cap 20 (see FIGS. 9-10). Thus, when a cap/syringe assembly 39 is placed into a socket 46 with the nozzle end 12 and cap 20 toward the socket 46, the cap/syringe assembly 39 is supported only by specific surfaces on the cap and socket.

Figure 16:
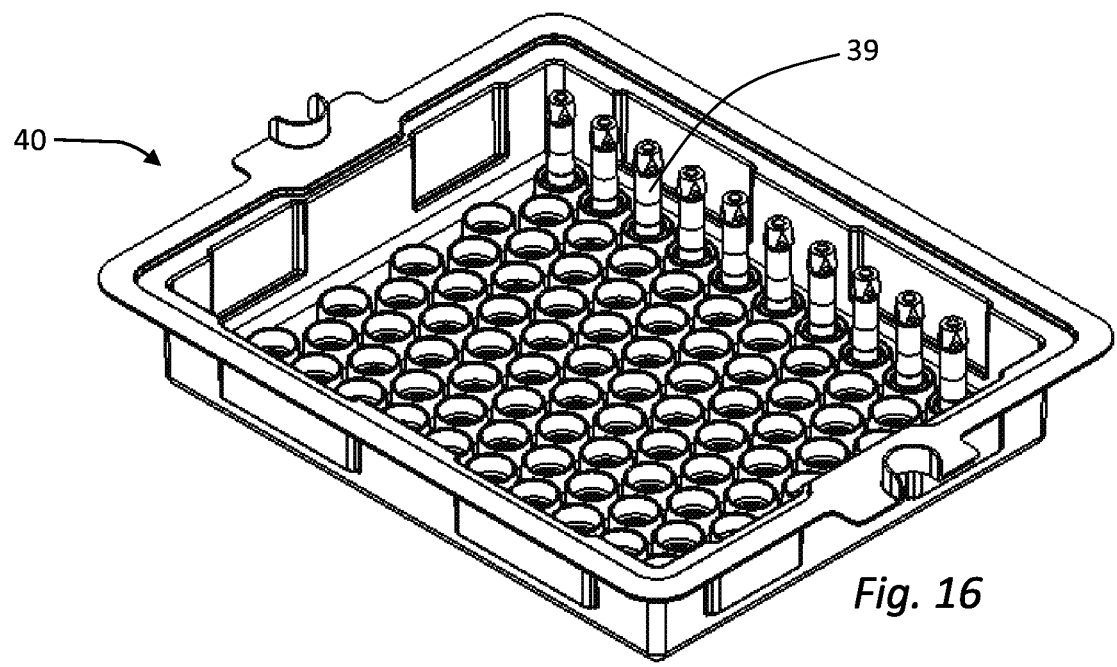
FIG. 16 is an isometric view of the filling tub of FIG. 12, when partially filled with cap and syringe assemblies.
Figure 17:
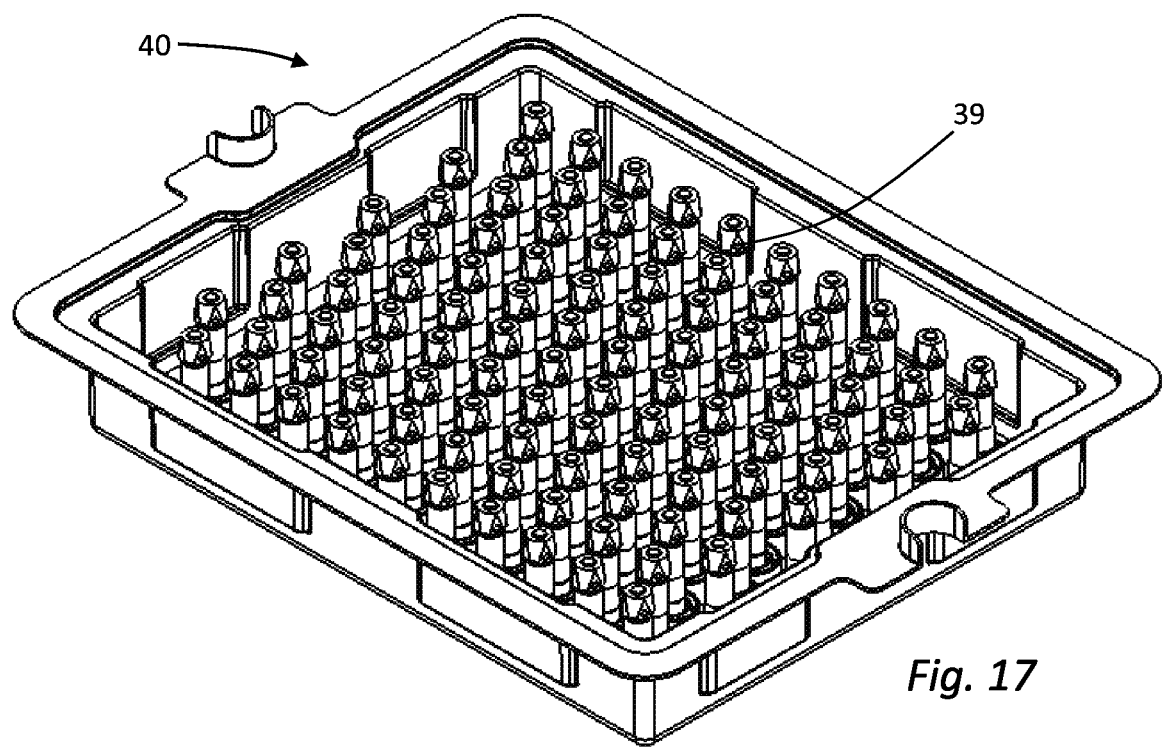
FIG. 17 is an isometric view of the filling tub of FIG. 12, when filled with cap and syringe assemblies.

In addition, the socket 46 includes an annular protrusion 52 surrounding a lifting bolt hole 54. The annular protrusion 52 is sized and positioned to engage with a terminal indentation 56 formed in the exterior surface of the cap 20 opposite the nozzle sealing extension 22. Thus, as shown in FIGS. 16-17, when a syringe and cap assembly 39 is placed into a socket 46, the syringe and cap assembly is supported solely by contact between the perimeter socket wall 48 and circumferential rim 50 and by contract between the annular protrusion 52 and terminal indentation 56.

The lifting bolt holes 54 provide for automated lifting devices such as rods or bolts associated with an automated filling mechanism to extend through the floor 44 of the filling tub 40 into contact with the terminal indentation 56 of a cap 20 to force a syringe and cap assembly 39 from the socket 46 during certain filling operations described in more detail below. When a cap and syringe assembly 39 is engaged with a lifting bolt, the terminal indentation 56 of the cap provides for secure and centered engagement with the lifting bolt.

Figure 18:
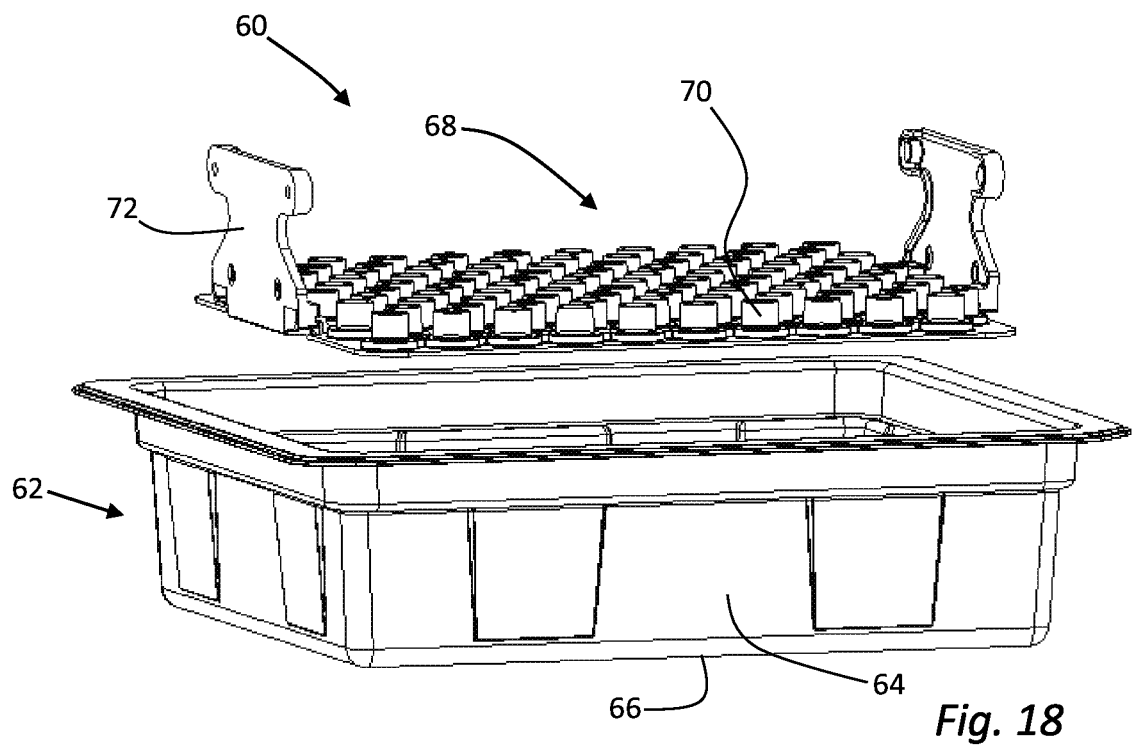
FIG. 18 is an isometric view of an alternative embodiment of filling tub featuring separate filling tub and nest assemblies.
Figure 19:
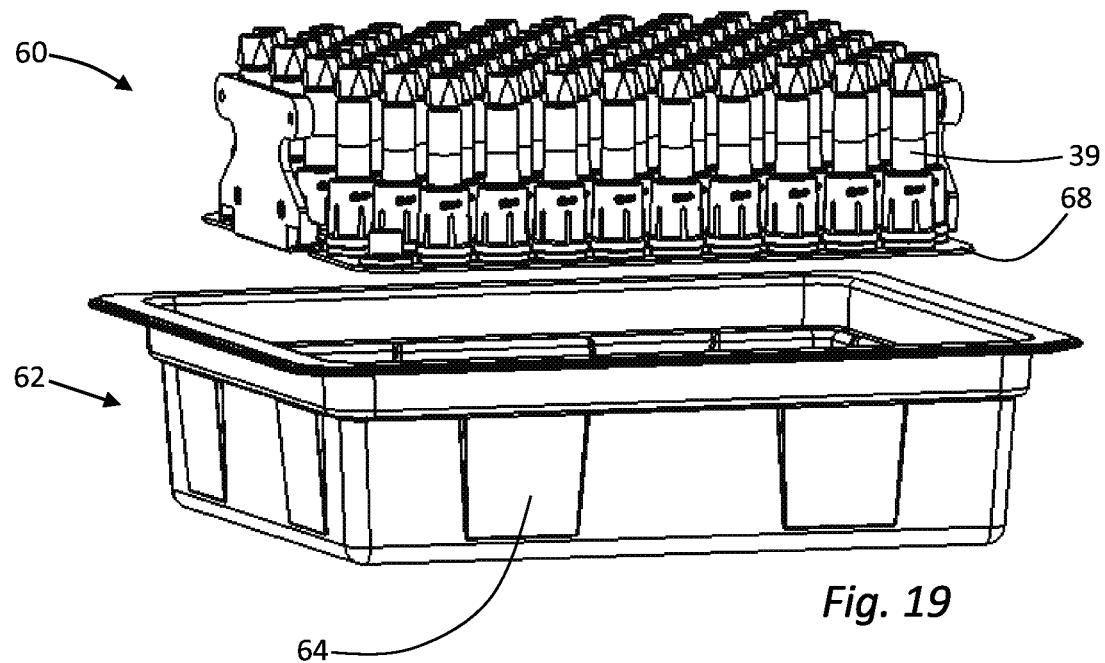
FIG. 19 is an isometric view of the filling tub of FIG. 18, when the nest is filled with cap and syringe assemblies.

As noted above, the filling tub 40 is provided as a single piece structure. Accordingly, selected exterior walls 42 of the filling tub 40 may be formed into reception hubs 58 which provide for an operator or more typically an automated machine to grip and manipulate the filling tub 40. An alternative embodiment is illustrated in FIGS. 18-19 which includes a separate filling tub and nest. The system 60 includes a filling tub 62 having exterior walls 64 and a floor 66. The filling tub 62 is sized to receive a separate nest 68 comprising multiple sockets 70. Each of the sockets of the separate nest 68 can be configured as described above and may include a perimeter socket wall, annular protrusion and lifting bolt hole, to support a syringe/cap assembly 39 with contact solely between specific surfaces of the socket and the outer surface of the cap.

Floor 66 of the filling tub 62 may in certain embodiments be perforated with corresponding lifting bolt holes if the filling system requires the automated removal of syringe/cap assemblies 39 while the nest 68 remains placed in the filling tub 62. Alternatively, the floor 66 of the filling tub 62 may be non-perforated with operations requiring lifting bolt engagement with a cap/syringe assembly 39 performed when the nest 68 is removed from the corresponding tub 62. The nest 68 may include reception hubs 72 to facilitate the automated or manual removal of the nest from the tub.

Figure 20:
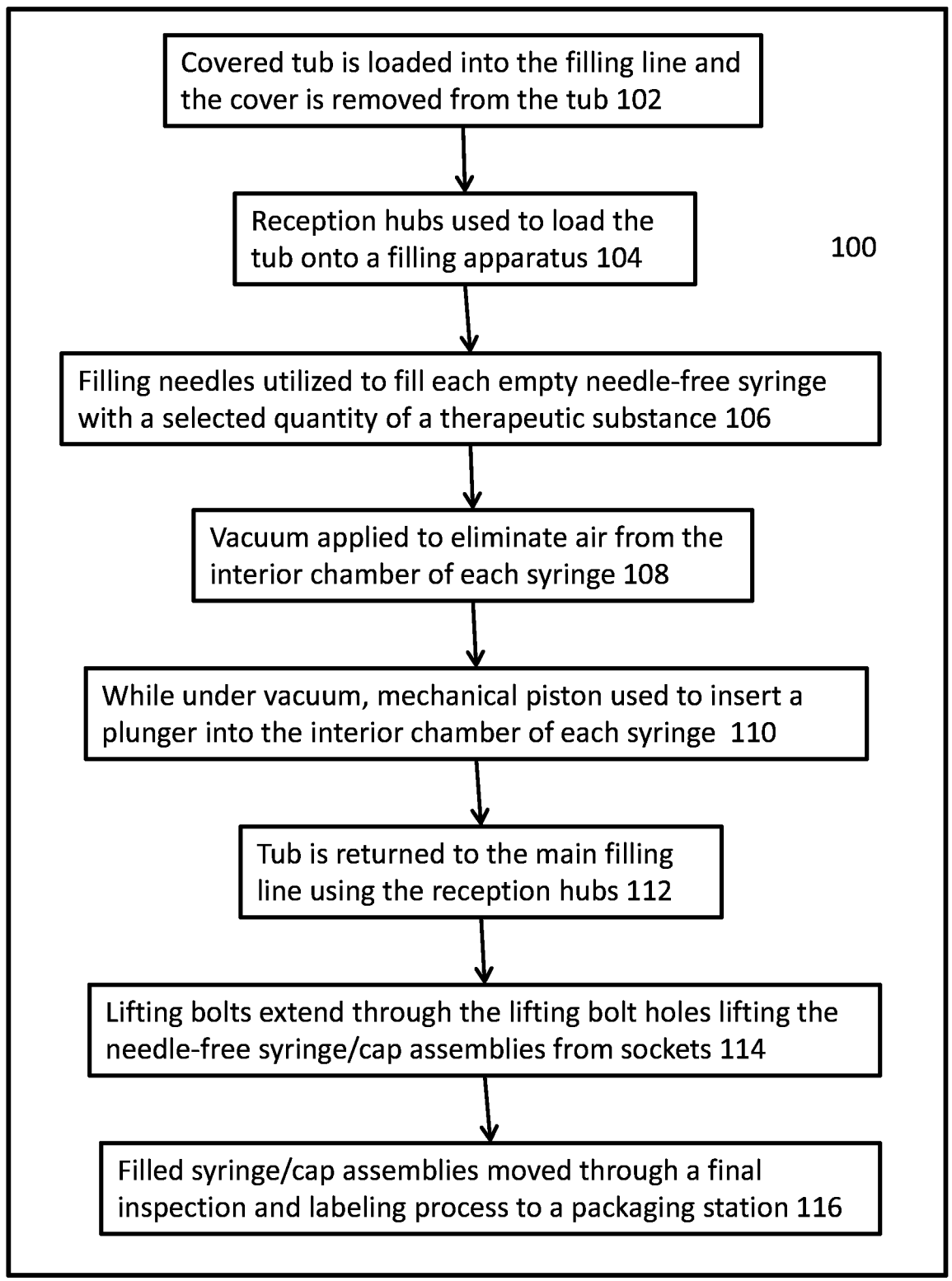
FIG. 20 is a flowchart representation of one embodiment of method as disclosed herein.

The apparatus described above facilitates the automated or semi-automated pre-filling of a select quantity of needle-free syringes. The various described apparatus may be adapted to any type of filling apparatus. One nonexclusive method 100 of filling a quantity of syringes is described below with respect to FIG. 20. The method is described with respect to the apparatus of FIGS. 1-17; however this method and similar methods are equally applicable to the alternative embodiments disclosed herein.

Prior to filling operations, the filling system is provided with one or more filling tubs 40 with some or all of the sockets 46 engaged with an empty syringe/cap assembly 39. The tub 40 is typically provided sealed with a cover, for example a sheet or film cover adhered to a top edge of the exterior walls to assure that the empty syringe/cap assemblies 39 do not become displaced during transportation to the filling system. Initially, the covered tub is loaded into the filling line and the cover is removed from the tub (Step 102). Then, the reception hubs 58 are used to load the tub 40 onto the filling apparatus (Step 104). Filling needles may then be utilized to fill each empty needle-free syringe with a controlled quantity of a therapeutic substance. The filling needles access the interior chamber 26 through the opening to the interior chamber 26 at the plunger end 14 of a needle-free syringe 10 (Step 106). After filling, a vacuum is applied to eliminate air from the interior chamber of each syringe (Step 108). While under vacuum, a mechanical piston may be used to insert a plunger 27 into the interior chamber 26 at the plunger end 14 of each syringe (Step 110). The vacuum differential pulls the plunger fully into place providing for the elimination of as much air as possible from the interior chamber 26 of the syringe.

After filling is complete, the tub 40 is returned to the main filling line using the reception hubs 58 (Step 112). Lifting bolts may then be caused to extend through the lifting bolt holes 54 in the floor of the filling tub 40 lifting the filled needle-free syringe/cap assemblies 39 from the sockets (Step 114). The engagement structures 18 of each syringe may then be engaged by a conveyor and each filled syringe/cap assembly 39 may be moved through final inspection and labeling processes to a packaging station (Step 116).

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the embodiments described herein have been particularly shown and described with reference to a number of possible variations, it would be understood by those skilled in the art that changes in the form and details may be made to various components or elements without departing from the spirit and scope of the embodiments and that the various embodiments disclosed herein are not intended to act as limitations on the scope of the claims. All references cited herein are incorporated in their entirety by reference.

What is claimed is:

1. A filling tub for needle-free syringes comprising:
   a one piece filling tub comprising a plurality of exterior tub walls and a floor;
   a plurality of lifting bolt holes extending through the floor, wherein each lifting bolt hole provides for a lifting bolt to extend through the floor; and
   a plurality of perimeter socket walls extending upward above the floor, wherein each perimeter socket wall defines a socket configured to receive and support a cap of a needle-free syringe body and cap assembly, and wherein each one of the lifting bolt holes extends into a corresponding socket.

2. The filling tub of claim 1 further comprising an annular protrusion formed in an individual socket of the plurality of sockets, wherein the annular protrusion surrounds the lifting bolt hole and the annular protrusion extends into the individual socket, said annular protrusion being configured to engage with the cap of the needle-free syringe body and cap assembly.

3. The filling tub of claim 1 wherein the plurality of perimeter socket walls are formed in and extend from the floor.

4. The filling tub of claim 1 further comprising a nest removably fit within the filling tub adjacent the floor, wherein the plurality of perimeter socket walls are formed in and extend from the nest.

5. A method of filling a needle-free syringe comprising:
   providing a syringe body and cap assembly comprising;
      a syringe body comprising a nozzle at a nozzle end, said nozzle defining an opening from the exterior of the syringe body to an interior chamber and a plunger opening at a plunger end of the syringe body, said plunger opening defining a second opening from the exterior of the syringe body to the interior chamber which plunger opening is located opposite the nozzle opening; and
      a cap engaged with the syringe body at the nozzle end, the cap comprising an interior surf ace which forms a fluid tight seal with the syringe body at the nozzle opening, and wherein the cap further comprises an exterior surface;
   providing a filling tub system comprising;
      a one piece filling tub comprising a plurality of exterior tub walls and a floor;
      a plurality of lifting bolt holes extending through the floor, wherein each lifting bolt hole provides for a lifting bolt to extend through the floor; and
      a plurality of perimeter socket walls extending upward above the floor, wherein each socket wall defines a socket configured to receive and support the cap engaged with the syringe body, wherein each one of the lifting bolt holes extends into a corresponding socket;
   engaging the syringe body and cap assembly with one of the plurality of sockets;
   filling the interior chamber of the syringe body to a select level with an injectable substance, wherein filling occurs through the plunger opening;
   inserting a plunger into the plunger opening of the filled syringe body.

6. The method of claim 5 further comprising engaging the syringe body and cap assembly with the socket such that contact occurs between an annular protrusion formed in the socket surrounding the lifting bolt hole and a terminal indentation formed in the cap.

7. The method of claim 6 further comprising:
providing the cap with a circumferential rim in the exterior surface; and
engaging the syringe body and cap assembly with the socket such that occurs only between the terminal indentation and annular protrusion and the circumferential rim and a socket wall when the cap and syringe body is engaged with the socket.

8. The method of claim 5 further comprising engaging the syringe body and cap assembly with a socket formed in the floor of the filling tub.

9. The method of claim 5 further comprising engaging the syringe body and cap assembly with a socket formed in a nest received in the filling tub adjacent to the floor of the filling tub.

10. The method of claim 5 further comprising:
providing the syringe body with a skin-tensioning ring surrounding the nozzle, the skin tensioning ring comprising an outer circumferential edge and an annular ridge formed at least partly around an exterior surface of the syringe body between the skin tensioning ring and the plunger end of the syringe body;
providing the cap with a plurality of grip structures formed in the interior surface of the cap; and
engaging both the skin tensioning ring and the annular ridge with the grip structures when the cap is engaged with the syringe body.

11. The method of claim 10 wherein the grip structures comprise an array of flexible fins arranged parallel to the skin tensioning ring and the annular ridge when the cap is engaged with the syringe body.

12. The method of claim 11 wherein each flexible fin extends only partially around a circumference of the interior surface of the cap.

13. The method of claim 10 further comprising:
providing the cap with a sealing extension; and
engaging the sealing extension with an inner circumference of the skin tensioning ring and with the exterior of the nozzle when the cap is engaged with the syringe body.

* * * * *